(12) United States Patent
Suh et al.

(10) Patent No.: US 8,921,539 B2
(45) Date of Patent: Dec. 30, 2014

(54) METHODS AND DEVICES FOR NUCLEIC ACID PURIFICATION

(75) Inventors: Chris Suh, San Jose, CA (US); Lee Hoang, Santa Clara, CA (US); Douglas T. Gjerde, Saratoga, CA (US)

(73) Assignee: PhyNexus, Inc., San Jose, CA (US)

( * ) Notice: Subject to any disclaimer, the term of this patent is extended or adjusted under 35 U.S.C. 154(b) by 112 days.

(21) Appl. No.: 13/434,656

(22) Filed: Mar. 29, 2012

(65) Prior Publication Data

US 2012/0252115 A1    Oct. 4, 2012

Related U.S. Application Data

(63) Continuation-in-part of application No. PCT/US2011/030232, filed on Mar. 29, 2011.

(51) Int. Cl.
*C07H 21/00*    (2006.01)

(52) U.S. Cl.
USPC .................................. 536/25.4; 435/283.1

(58) Field of Classification Search
USPC .................................. 536/25.4; 435/283.1
See application file for complete search history.

(56) References Cited

U.S. PATENT DOCUMENTS 7,488,603 B2 *    2/2009    Gjerde et al. ............... 436/177
8,053,247 B2 *    11/2011    Feuerstein et al. .......... 436/174
8,377,715 B2      2/2013    Suh et al.

* cited by examiner

*Primary Examiner* — Ardin Marschel
(74) *Attorney, Agent, or Firm* — Sue S. Kalman

(57) ABSTRACT

The invention provides pipette tip columns and automated methods for the purification of nucleic acids such as plasmids from unclarified cell lysates containing cell debris as well as methods for making and using such columns. The columns typically include a bed of medium positioned in the pipette tip column, above a bottom frit and with an optional top frit.

6 Claims, 5 Drawing Sheets

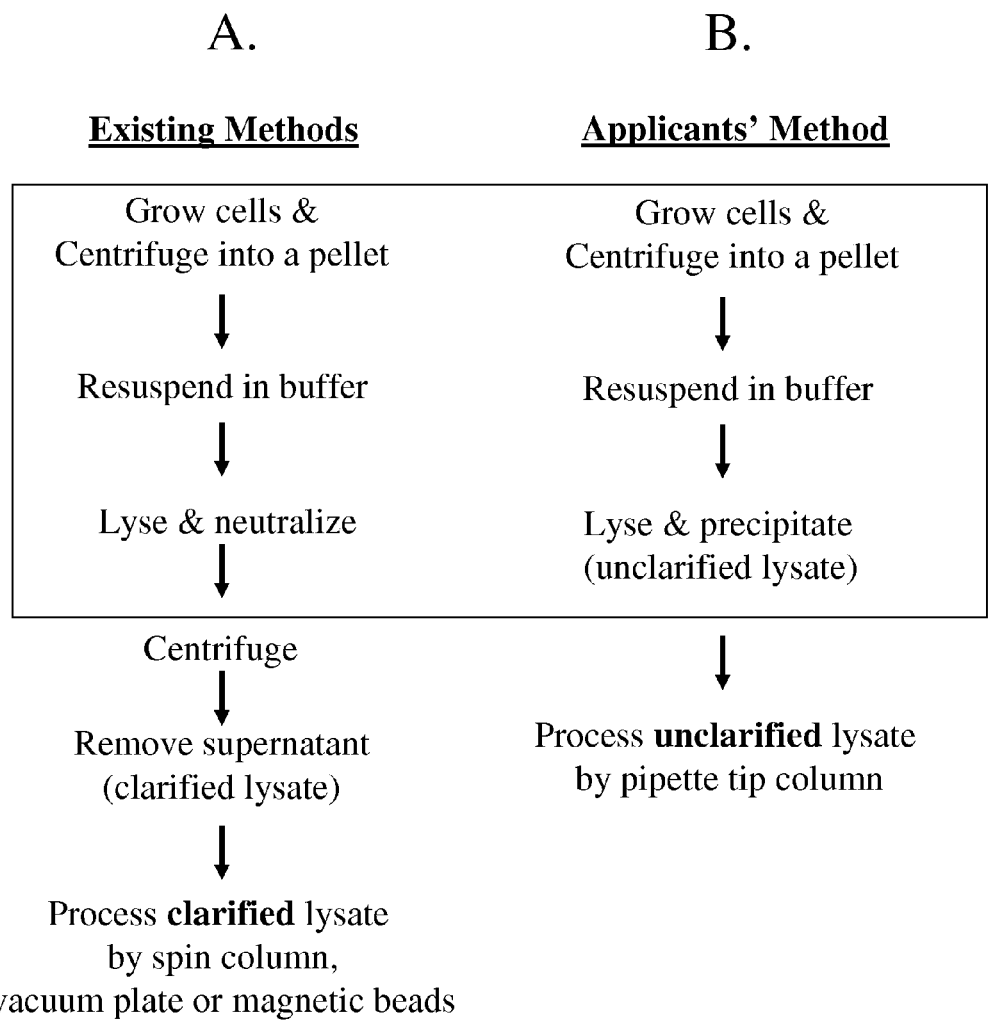
Figure 5. Method of the invention versus existing methods

US 8,921,539 B2

METHODS AND DEVICES FOR NUCLEIC ACID PURIFICATION

CROSS REFERENCE TO RELATED APPLICATIONS

This application is a continuation-in-part of International Application No. PCT/US 11/30232 filed Mar. 29, 2011, the disclosure of which is incorporated herein by reference in its entirety for all purposes.

FIELD OF THE INVENTION

This invention relates to methods and devices for sample preparation, such as separating (i.e., extracting or purifying) nucleic acids such as DNA and RNA, and more particularly, circular self-replicating elements such as plasmids, BACs, YACs, cosmids, fosmids and bacteriophage vectors such as M13. The device and method of this invention are particularly useful in DNA vector purification by pipette tip column. The device and method of this invention are particularly useful in purifying plasmids from unclarified cell lysates and other samples containing particulates and cell debris.

BACKGROUND OF THE INVENTION

Commercially-available formats for nucleic acid purification include spin columns, magnetic beads in a tube or the use of vacuum to draw liquids through a column or plate. In these formats, nucleic acids are isolated as follows. The cells are grown in a suitable medium, the culture is centrifuged to collect the cells and the growth medium is discarded. Next, the cells are lysed, e.g., with an alkali solution followed by the addition of a neutralizing solution. Traditionally, a second centrifugation step is performed after lysis to pellet the cell debris and the nucleic acids are purified from the supernatant.

When the spin column format is employed, several additional centrifugations are performed. Because all these methods require at least two centrifugation steps, they are time-consuming, laborious and difficult to fully automate. They require significant human intervention and cannot be performed in a walk-away fashion. Methods involving removal of the particulate from the cell lysate by filtration are not reliable. There exists a need for automated, high-throughput nucleic acid purification in a pipette tip column format. Furthermore, there exists a need for purifying plasmids from unclarified cell lysates and other samples containing particulates and cell debris.

SUMMARY OF THE INVENTION

A highly automatable method for purifying nucleic acids in a pipette tip column format was developed. An advantage of the instant invention is that nucleic acids are purified after the lysis step without the need for cell debris removal. Nucleic acids are purified directly from an unclarified lysate in an automated fashion. The method is particularly well suited for purification of plasmids.

BRIEF DESCRIPTION OF THE FIGURES

FIG. 5 is a flowchart comparison of invention versus existing methods.

DETAILED DESCRIPTION OF THE INVENTION

Figure 1:
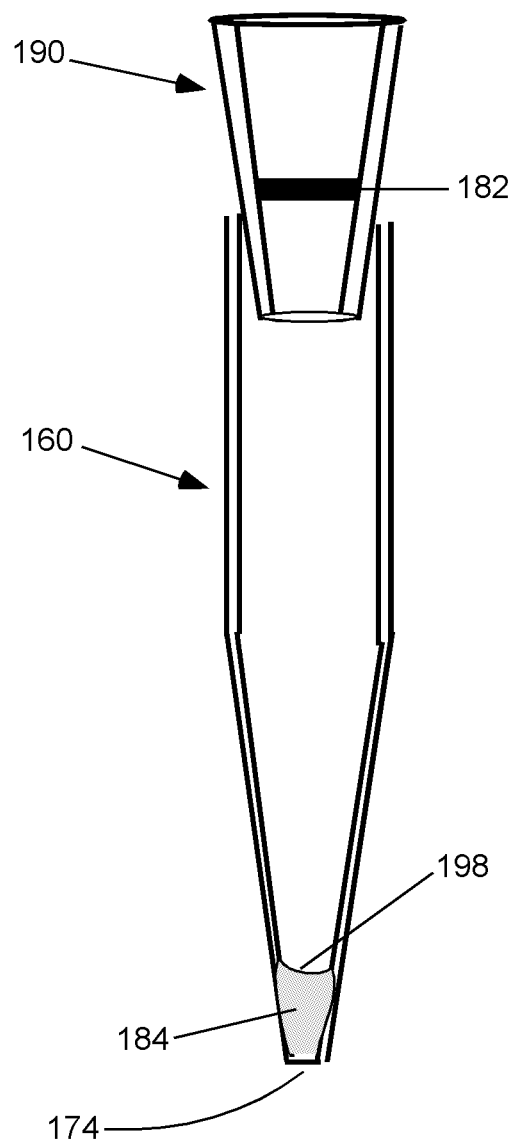
FIG. 1 depicts an embodiment of the pipette tip column.

This invention relates to methods and devices for extracting nucleic acids, particularly plasmids from a sample solution. In U.S. patent application Ser. No. 10/620,155, now U.S. Pat. No. 7,482,169, incorporated by reference herein in its entirety, methods and devices for performing low dead column extractions are described. In U.S. patent application Ser. No. 12/767,659, also incorporated by reference herein in its entirety, columns and methods for purification of DNA vectors are described.

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, specific examples of appropriate materials and methods are described herein.

Definitions

In describing and claiming the present invention, the following terminology will be used in accordance with the definitions set out below.

Automated methods are defined herein as methods not requiring human interaction.

The term "bed volume" as used herein is defined as the volume of medium or solid phase within the column. The term "interstitial volume" of the bed refers to the volume of the bed of extraction medium that is accessible to solvent, e.g., aqueous sample solutions, wash solutions and desorption solvents. This includes the space between the beads as well as any volume taken up by the pores within the beads. The interstitial volume of the bed represents the minimum volume of liquid required to saturate the column bed.

The term "dead volume" as used herein with respect to a column is defined as the interstitial volume of the extraction bed, membrane or frits, and passageways in a column. Some preferred embodiments of the invention involve the use of low dead volume columns, as described in more detail in U.S. Pat. No. 7,482,169.

The term "elution volume" as used herein is defined as the volume of desorption or elution liquid into which the analytes are desorbed and collected. The terms "desorption solvent", "elution liquid", combinations thereof and the like are used interchangeably herein.

The term "frit" as used herein is defined as porous material for holding the medium in the column. In preferred embodiments of the invention, the frit is a thin, low pore volume, large pore screen.

The term "pipette tip column" as used herein is defined as any column containing a solid phase that can engage a pipette, syringe or liquid handler, either directly or indirectly. The term, "pipette tip column" is not limited to columns manufactured in pipette tips. Rather the column can have any shape or geometry as long as it is capable of engaging a pipette, syringe pump or liquid handling robot. Pipette tip columns can be positioned in a rack or incorporated into a plate.

The term "lysis" or "lysed" is a process by which cell are treated to break the cell walls and release the nucleic acids.

The term, "plasmid" is defined as an extra-chromosomal, self-replicating nucleic acid molecule. A plasmid can be a single or double stranded and can be comprised of DNA or RNA. Cosmids, fosmids, BACs and YACs are considered to be within the purview of the plasmid definition.

The term, "unclarified lysate" refers to a cell suspension which has been subjected to lysis.

The term, "gentle mixing" refers to a flow rate in the range of 0.1 ml/min-10 ml/min for at least two cycles using a wide-bore pipette. The term, "cycle" as used herein is defined as a single aspirate/expel step.

It is a goal of the invention to develop an automated, high-throughput method for plasmid purification in a pipette tip column format. Commonly used commercially-available formats for plasmid purification include spin columns, vacuum plates and test tubes. However, there are currently no commercially-available, automated high-throughput methods performed in a pipette tip column.

In the invention described herein, plasmid DNA can be purified from any source. In some embodiments, the plasmids can be purified from biological sources such as cells. The cells can be eukaryotic or prokaryotic. In other embodiments, plasmids can be purified from a mixture of nucleic acids or from a gel. Excellent yield and concentration can be obtained using this method, e.g., a yield of up to 30 µg from a 1.4-mL *E. coli* culture harboring a low copy number plasmid.

Plasmids are purified from multiple samples simultaneously in an automated manner for example, with a robotic workstation or electronic pipette. Typically, automated methods are performed with pipette tips and 96-well plates arranged in a 9 mm center-to-center format. However, other formats are possible, e.g., 4.5 mm center-to-center or 18 mm center-to-center. It is a goal of the invention is to reduce the number of manual processing steps used in methods for purifying plasmids. That is, it is desirable to perform high throughput separation of plasmids with minimal operator intervention. However, embodiments of the invention also include purification of plasmid DNA from a single sample.

To develop a robust method for purifying plasmid DNA from cells, experiments were performed in which plasmids were purified from *E. coli* cells. After the cells are grown, they are collected by centrifugation and the growth medium is discarded. The next step for purifying nucleic acids is cell lysis. Lysis can be carried out by a number of means including the use of chemicals i.e., detergents or by mechanical/physical means, such as sonication.

Currently, the predominant commercially-available formats for plasmid purification are spin columns, magnetic beads and vacuum plates. In these methods, cell debris is removed by centrifugation after the lysis and neutralization steps to obtain a "clarified lysate" from which nucleic acids are purified (FIG. 5A). Removal of cell debris is most often accomplished by centrifugation but can also be done by filtration in some vacuum plate methods. However, because it is difficult to fully automate the steps of centrifugation and filtration, it is time-consuming and laborious to purify nucleic acids from a large number of samples simultaneously.

Formats for plasmid preparation via vacuum include individual columns and multi-well plates. Even after producing a clarified lysate, these methods are not well suited for automation. Some protocols recommend turning off the vacuum while adding reagents, which requires operator involvement. Additionally, differences between samples can cause differential column pressures between columns or wells within the plate so an operator is often needed to ensure the vacuum manifold seal is maintained or that the liquid sample flow occurs evenly through all the wells of the plate. Since spin columns require a series of centrifugation steps, they are not amenable to automation without special equipment. Magnetic beads are expensive and require repeated shake and aspiration steps, which makes their use difficult to automate. Magnetic beads or other bead suspension methods that do not first remove the cell debris are not reproducible and are difficult to automate.

An advantage of the instant invention is that plasmids can be purified in parallel, up to 96 samples at a time without operator involvement. With proper instrumentation, multiple plates of 96 samples can be processed simultaneously.

One point of novelty of the invention is that the automated purification procedure can begin with resuspension of the cell pellet. That is, nucleic acids are purified directly from an unclarified lysate in an automated fashion (FIG. 5B). There is no need for cell debris removal. Because the method is performed on an unclarified lysate, fewer disposables are needed and consequently, the cost is lower.

Although it was desirable to eliminate the cell debris removal step and isolate nucleic acids directly from an unclarified lysate, it was technically quite difficult to accomplish. Pipette tip columns provide a unique set of technical challenges not present in other formats such as spin columns or vacuum plates. For example, when using a liquid handling robot, the pressure available to push liquids through the columns is very low compared to centrifugation or vacuum. In addition, the unclarified lysate is much more heterogeneous, viscous and gelatinous than a clarified lysate. It contains all cellular contents including cell debris, genomic DNA, particulates and liquid. It is surprising that plasmid DNA can be effectively purified from such a heterogeneous mixture.

An experiment was performed to compare the viscosity of the unclarified lysate to that of a clarified lysate. An overnight culture of *E. coli* harboring a plasmid was subjected to centrifugation, resuspension, lysis and precipitation. A clarified lysate was made from half the mixture and the viscosity was compared to the corresponding unclarified lysate. For each sample, the efflux time was measured using a size 400 Cannon-Fenske Routine Viscometer. The efflux time is the time it takes for the solution to travel between two points within a glass tube. The efflux time for the unclarified lysate was almost twice as long as that for the clarified lysate (2.17 seconds vs. 1.18 seconds). The kinematic viscosity was calculated to be 2.6 centistokes for the unclarified lysate compared to 1.4 centistokes for the clarified lysate.

In U.S. patent application Ser. No. 12/767,659, we described our first approach to solving these problems. Although the invention described in U.S. patent application Ser. No. 12/767,659 was an advance over other methods, the results obtained were still inconsistent. Sometimes, the columns plugged with particulates contained in the unclarified lysate. In some cultures, the particulates seemed to be greater in mass and all or most of the columns plugged. Even if the procedure worked without incident at times, the recovered, purified vector performed well for sequencing but sometimes couldn't be used effectively for transfection or transformation. Another problem observed was that the $A_{260}$ was artificially high at times, particularly when the plasmid was present in a low or medium copy number. After plasmid purification, the concentration was measured by UV and also by a semi-quantitative measurement of the intensity of the plasmid band on an agarose gel. The comparison of these two methods suggested that something present in the sample might be co-purified with the plasmid, causing the $A_{260}$ to be artificially high.

In the instant application, these problems were solved making the method significantly more robust and reliable. Better sampling and purification methods were developed along with methods that allow scale-up in an automated format. The quality and purity of the product was improved making it useable for a greater variety of downstream applications.

To address the problem of random column plugging and increase the reproducibility of the method, we examined and developed an entirely new sampling procedure. It was discovered that the amount and type of particulate in unclarified lysate varied depending on a number of parameters including medium, strain, replicon, growth time and conditions. It turned out that the distribution of the cell debris present in the sample differed dramatically between samples. Sometimes the debris was distributed more or less throughout the sample, sometimes the majority of the debris floated, but in other instances a portion of the cell debris sank. This variability seemed to be one reason the method was not reproducible and that sometimes the columns plugged. Another reason seemed to be the amount of mass particulate varied tremendously from sample to sample. In some cases, the floating mass of particulate appeared to take up a large part, or even most of the sample.

Yet to recover the maximum amount of plasmid in the lysate, it was important to sample all of the liquid, regardless of where and how much particulate mass was in the sample. Particulate masses present in the lysate contained liquid that appeared entrained and occluded. There did not appear to be active exchange of the occluded liquid with the other liquid in the sample.

Generally, in a suspension of particulates with liquid, the liquid can move freely throughout the sample. But when masses or globs of particulate accumulate in a sample in a stable form, free movement of the liquid within the mass is halted. The mass of particulate is almost like a large hydrated bead; there is no active transport of liquids but only diffusion. The masses looked globular and gel-like. It was speculated that plasmid contained in these globules would be unreachable unless the masses were broken up because active transport of liquid in and out of the mass would be limited. In U.S. patent application Ser. No. 12/767,659, passing these masses through the column broke up the masses and allowed capture of the plasmids. The only way to capture plasmid contained in the entire sample, including the sample within this occluded liquid, was to pass the entire sample through the column.

Development of an Improved Sampling Method

A novel sampling method was developed to improve plasmid isolation from the unclarified lysate. First, the solutions were changed. In patent application Ser. No. 12/767,659, we used a lysis solution followed by a neutralization buffer comprised of a chaotropic salt, a salt and an acid. However, it was determined that it was more effective to use two solutions sequentially. The lysis solution was first followed by a solution for neutralization (acid and salt) and then a second solution containing the chaotropic reagent. When a solution containing salt and acid were added prior to the chaotropic salt solution, the $A_{260}$ more accurately matched the plasmid concentration obtained by the agarose gel band intensity. In addition, the amount of precipitate or cell debris generated seemed to be more uniform.

However, this did not solve the reproducibility and plugging issue. There were still large amounts of particulate masses in the sample that contained entrained liquid. In some cases, these masses floated, while in other cases, the masses precipitated. Some particulate remained in suspension of the sample but depending on the cell growth conditions and time, the mass of cell debris appeared to make up about 20-50% of the sample.

In commercially-available methods, the sample is centrifuged at this stage and the supernatant (the clarified lysate) is used from plasmid capture. Once the sample has been centrifuged, the liquid is very easy to process using spin columns or plates.

In the unclarified lysate used in the invention, it is likely that the actual solids content in the masses was only a very small portion of the sample. But having a substantial proportion of the sample entrained or occluded within the floating or sinking masses seemed to be the major issue. The liquid entrained within the mass of solid did not appear to be available for capture unless there was active transport of the liquid to the resin in the column.

A second change made to the sampling procedure was that only a portion of the sample was aspirated and expelled. Instead of aspirating the entire unclarified lysate, only a portion was sampled. Quite unexpectedly, it was determined that as little as 10% of the total volume could be repeatedly aspirated and expelled and the yield was not affected provided the number of cycles of liquid traveling through the column was increased. The term, "cycle" as used herein is defined as a single aspirate/expel step. Without being bound by theory, it is possible that the mass of particulate broke up and reformed with each expulsion of the liquid back into the sample thus releasing or exchanging some of the entrained liquid. It did not seem possible that diffusion of the plasmid from the occluded liquid could occur because the distance to diffuse would be several millimeters and could even be more than a centimeter in some cases.

Several side-by-side experiments were performed. Plasmid recovery was measured by $A_{260}$ and by the plasmid band intensity on a slab gel. A side-by-side comparison of the method of the invention with commercial spin columns was performed. Also included in the side-by-side comparison was the old method of sampling where the entire liquid sample was passed through the column. The results from the slab gel band measurement showed that as the number of capture cycles was increased, the two pipette tip column methods gave comparable results while the spin columns gave slightly higher yield.

The UV measurements were inconsistent. At times, they gave comparable results for all three methods while at other times, the pipette tip columns gave much higher results. Flow rates were adjusted to be slower until the all three methods gave UV results that agreed with the slab gel band intensity results. From this, it was surmised that at least part of the plasmid quality problem discovered earlier was due to the capture of sheared genomic DNA.

The experiments showed that sample volumes as low as 10% of the total volume in the well could be sampled and still get adequate sample recovery. As high as 90% of the volume could be sampled while still eliminating plugging of the column and get good recovery of the plasmid. Preferably, between 10 and 90% of the sample volume can be sampled, more preferably 20-80% of the volume can be sampled, more preferably 30-70% of the volume can be sampled, more preferably 40-60% of the volume can be sampled, most preferably 35-50% of the unclarified lysate volume can be sampled. These results were unexpected and surprising in light of the fact that the particulates were often globular and appeared to have liquid sample entrained which had appeared to prevent capture of the plasmid within this liquid volume.

In some embodiments, the sampling procedure was modified to include the addition of an aspirate and expel step prior to plasmid capture. Air is drawn slowly through the pipette tip columns attached to the robotic head. Then the columns are submerged in the sample and the air is slowly expelled through the columns into the unclarified lysate. The step caused the bulk of the particulates to float which more effectively kept them farther away from the open lower end of the column during the subsequent aspirate/expel cycles used for plasmid capture.

Improved Plasmid Quality

In U.S. patent application Ser. No. 12/767,659, removal of the interstitial liquid from columns by vacuum or air pressure was described. Only a short duration of vacuum or air pressure is required to remove this bulk (interstitial) liquid: 0.1-1 minute or even between 5 and 30 seconds depending on the force of the vacuum or air pressure.

In the methods described in U.S. patent application Ser. No. 12/767,659, bulk liquid was removed and the plasmid or nucleic acid was recovered from the column by passing water or buffer through the column. The quality of the plasmid was quite good and it was suitable for downstream processing such as sequencing, mutation analysis, etc. However, it was discovered that the plasmid recovered from this process could not be used successfully for transfection. The gels showing the recovered plasmid indicated pure and concentrated plasmid yet, transfection frequency was very low.

The procedure described in U.S. patent application Ser. No. 12/767,659 yielded a suitable quantity of plasmid DNA that performed well in DNA sequencing, however it was discovered that the baculovirus transfection and bacterial transformation efficiency was unexpectedly low. Initially, it was thought that the low transfection frequency was due to contamination with protein, guanidinium or perhaps endotoxin. Endotoxin was measured as described below and protein was measured by absorbance at 280 nm and these were ruled out as contaminants. It was considered that there could be a nucleic acid contaminant in the recovered plasmid such as genomic DNA or RNA. However, it wasn't possible to directly measure the genomic DNA or RNA contamination.

Finally, it was suggested that a measurement should be performed of residual solvent in the recovered plasmid since the Wash buffer contained ethanol. The columns appeared to be free of solvent before the elution step and there was no indication that the recovered plasmid contained any ethanol. The interstitial liquid in the column prior to elution appeared by visual inspection to be completely removed.

A Carl Zeiss single optic stand held refractometer was used to measure the alcohol content in the purified plasmid. Aqueous standards containing known concentrations of ethanol were prepared and an analysis of the recovered plasmid was performed on several samples. Surprisingly, the samples of purified plasmid contained considerable amounts of ethanol, in the range of 5-15% (vol/vol). This result was surprising because it was thought that ethanol would prevent efficient elution of the plasmid from the column. There is no alcohol in the elution solvent in order to get efficient elution. The presence of ethanol was also surprising because a mini-prep performed using a commercially-available spin column method produced a final alcohol content in the recovered plasmid in the 2-3% range. So clearly, something about the columns or the method caused the residual ethanol to be present.

It was known that as the particle size of the resin used in the pipette tip columns was large. This was because the frit pore size of the columns had been increased to reduce plugging and therefore the particle size of the resin was also increased so that it did not fall out of the column. Without wishing to be bound by theory, it was known that the resin can contain pores to increase surface area and facilitate plasmid capture. Unfortunately, the resin appeared to retain much more solvent than the spin columns, possibly due to its higher porosity and greater surface area. In addition, the centrifugal force applied to spin columns is probably quite efficient at vacating any liquid remaining in the column. This retained solvent may have contributed to the higher percentage of ethanol present in the eluted plasmid. Alternatively, the higher percentage of alcohol obtained from the pipette tip columns and method could have been due to some other unknown phenomena.

Several different remedies were tested to solve the problem of residual organic solvent in the purified plasmid. The first method evaluated was simply to lift the columns out of the wash solution and pass air back and forth through the column with the robotic pipette head. Even though the resin bed appeared to be equally wet at the beginning and end of the process, the amount of organic solvent in eluted plasmid decreased. While this method would likely work if the back and forth flow was performed with adequate number of cycles, it was not preferred because it added too much additional time to the method.

Other options to pass air through the columns were considered. Air could be forced through the columns by positive pressure however, this would require an additional apparatus be designed and built. Vacuum could be used, not only to remove bulk liquid, but as an additional step implemented to move air through the columns after the bulk liquid had been removed from the interstitial space. A vacuum pump rated to pull 4 cubic feet per minute through the pump at zero vacuum was used to pull air through columns under a number of different conditions.

These first experiments involved forcing air through set of 80 μL bed columns in a 96 well format and measuring the effect of total air through the system. After 1 minute and removal of the interstitial liquid, the total air pulled was measured to be 4 cubic feet. The measurement was performed by taking a venturi-type air flow meter and connecting the meter to the vacuum in the reverse connection so that the air pulled through the meter was measured (rather than the normal measurement of air pushed through the meter). The initial experiments showed that the liquid was pulled through the column. After the initial liquid was removed, air appeared to be pulled through the columns.

The vacuum method was investigated by depositing the pipette tip columns into a vacuum station on the robot deck and passing air through the columns using vacuum. An oil vacuum pump (0.5 horsepower) was used to pull a vacuum of 4 ft$^3$/min through the columns. This use of vacuum is quite distinct from the traditional use of vacuum. Traditionally, vacuum is used to pull liquid solutions through plates or columns. After the solution passes through the plate or column, the vacuum is turned off because the task has been accomplished. In the case of the instant invention, the wash solution had already been passed through the columns and the vacuum is used simply to draw air through the columns.

However, when measurements were performed with an air flow bubble meter (also connected in reverse) on individual wells, it was determined that the air flow after the interstitial liquid was removed from the column was not consistent from column to column. In fact, it was found that no air, or very little air was flowing through many of the columns while other columns had significant air flow-through. Upon further investigation, it was determined that once the initial liquid had been removed from the columns, the vacuum seal formed for each column was inconsistent. Analysis by refractive index of the elution solvent pulled through a number of columns indicated there was a correlation between the quality of the vacuum seal and the amount of ethanol recovered with the solvent. That is, those columns with a poor seal contained more ethanol while those columns having a good seal contained less. However, there was no difference in appearance of the individual columns. They all looked as though the interstitial liquid had been removed and they all looked equally wet with surface liquid.

The next process tried was use of a 96-well aluminum heating block oven and a forced air oven. The ovens were set to 37-42° C. After final wash and expulsion of as much liquid as possible, the columns were placed in the ovens for 10-30 minutes. Again, the columns appeared wet after incubation in the ovens however, the ethanol concentration was reduced to as low as 5%. This result was encouraging however, the time required was still longer than desired.

It was necessary to build a custom 96-well vacuum block. To test the effectiveness of the vacuum block, it was necessary to build two additional air flow measurement apparatus. It was not possible to measure the air flow by seeing the liquid flow through the columns. The air flow had to be measured directly. The first apparatus was a cover for the vacuum block that was attached to an air gauge and used to measure air flow through the entire block. The air gauge (King Instrument Company, Part No. 75201102C17) was actually used in reverse. That is, air was pulled through the top of the gauge rather than being pushed through the bottom of the gauge as it was designed. Using this cover, a reading greater than 0.4 cfm was achieved with the pump and block being tested. Lifting the block from the vacuum manifold showed that there was a good seal between the vacuum block and its manifold base.

After redesigning of the vacuum block, the air pulled through by vacuum after the interstitial liquid was removed became more consistent between columns. More ethanol was found when the air flow was slower, even though the columns appeared the same regardless of the airflow duration. It turned out, the vacuum generally pulled air through the column on an equal basis although the columns on the outside of the vacuum block still had higher flow than the center columns. Presumably this simple design permitted vacuum to pull the interstitial liquid through the columns, but once this was done, the vacuum applied to the columns was insufficient to apply uniform vacuum to all of the individual columns.

Several vacuum blocks were built before an adequate block design was found. The first block built had 96 positions on the top for the columns and an open architecture on the bottom of the block. The air flow through the block seemed adequate. However, it was not possible to get a tight seal when this block was tested with the cover. It seemed possible that while the total air flow may have been adequate, the air flow across the individual columns could differ dramatically.

A second custom apparatus was built to test the vacuum through individual columns seated in the vacuum block. In this case a bubble meter tube for measuring gas flow out of a packed bed gas chromatograph was modified to measure vacuum. A Wilmad LabGlass 10 mL gas flow bubble meter was adapted to measure air flow through the individual columns. As with the other gauge, the vacuum was applied to the top of the meter tube, leaving the tube fitting open that would normally have been the inlet from the gas chromatographic column. 96 columns were placed in the block and the air flow through each column was measured. Using this gauge, it was discovered that flow was not even between the columns. To solve this problem, the vacuum block was redesigned to have a gasket seal around each column.

The design of the column seal(s) proved to be difficult. The seal had to be tight enough to seal all of the columns routinely and adequately. But the column had to be easily placed into the apparatus and it must be possible to remove the columns from the block without the block being pulled up along with the columns. The seal cannot be so tight as to prevent engagement of the columns by the robotic head. If the columns seals were too tight, attempting to remove the columns from the block could result in the block being lifted with the columns. So the seal could not be too tight. After several redesigns the block applied vacuum evenly through all the columns. Interestingly, it was not possible to determine whether air flowed through a particular column or not by visual inspection. Only the custom measurement tools could provide this information.

The redesign of the vacuum block provided a tighter seal around each column while still allowing the columns to be removed from the block. After the redesign, experiments were performed to determine how much airflow was needed to remove the residual ethanol from the column. The level of vacuum and the vacuum duration were varied. In another set of experiments, the number of columns to which vacuum was applied was varied while keeping the vacuum level constant. In all experiments, the column appeared dry by visual inspection before and after the vacuum was applied. The results showed that for 96 columns with an 80 µL bed volume, a vacuum of 4 cubic feet per minute (CFM) applied for between 1 to 20 minutes (above and beyond the vacuum needed for removal of the interstitial liquid) was needed to lower the ethanol concentration of the eluent to 0-5%. This corresponds to an amount of 4-80 cubic feet of air passed through 96 columns.

The next step involved testing the vacuum procedure for removal of the organic solvent present in the wash solution. Liquid containing various amounts of ethanol was cycled through the columns. The columns were placed in the vacuum block and vacuum was applied for varying amounts of time. The columns were eluted with water, the eluant collected and the refractive index was measured for organic solvent concentration. After the solvent removal step, the columns still appeared wet by visual inspection. To maintain the highest possible throughput, it was desirable to find the shortest possible vacuum duration that resulted in purified plasmid having acceptably low alcohol content. Although the solvent drying step is an additional step to the process, if a very strong vacuum is used, the columns can be dried more quickly without sacrificing throughput.

Depending on the vacuum applied and the air flow through the individual columns, the "drying time" can be between 30 seconds and 20 minutes, but preferably between 2 and 5 minutes. Drying time is defined as the time that vacuum or air flow is applied after the removal of the bulk liquid (which can also be done by vacuum or air). Based on these experiments, a vacuum duration was determined for which the eluant contained an acceptable amount of ethanol. Preferably, the percentage of ethanol in the purified plasmid is less than 10%, less than 9%, less than 8%, less than 7%, less than 6%, less than 5%, less than 4%, less than 3%, less than 2% or less than 1%. Less than 5% solvent was preferred and less than 3% was most preferred.

In other embodiments with longer drying conditions, it is possible to dry the columns completely prior to elution of the purified plasmid. However, good results were obtained when the solvent was substantially removed and the columns were not dried completely after the final wash and prior to elution.

Implementation of the solvent removal step affected the reproducibility of the elution step. For example, when 80 μL bed silica columns were subjected to vacuum to remove the organic solvent present in the wash, 130 μL of water was used for the elution step and only 80-90 μL of liquid was collected. This result indicated that a significant portion of the water was trapped in the dead volume of the pipette tip column.

To help mitigate this problem, the elution step can be modified. An additional step can be added at the end of the procedure to maximize the elution volume. Air can be taken up by the robotic pipetting head after the solvent removal step and prior to engagement of the columns for elution. This added air is then expelled after expulsion of the purified plasmid to get as much liquid as possible out of the column.

Yield can also be increased by incubating the elution solution on the column prior to expulsion. As an example, the elution solvent can be aspirated and incubated on the column for 5 minutes prior to expulsion.

Endotoxin Assay

To test the quality of different plasmid DNA purification processes, an endotoxin test was carried out. Plasmid DNA was purified in triplicate from *E. coli* pellets as described, above. Additionally, plasmid DNA was purified in duplicate using a spin column method (Qiagen Cat. #27104) according to the manufacturer's protocol. The plasmid DNAs were tested using a ToxinSensor Chromogenic LAL Endotoxin Assay Kit from Genscript (Cat. L00350C). Using the supplied endotoxin controls a standard curve was generated, and the amount of endotoxin in the plasmid DNA preparation was quantified. In all cases, endotoxin was measured to be less than 0.01 endotoxin units per microgram of DNA, well within the acceptable levels for transfection experiments (Table 1).

the invention with nucleic acid recovery in this range can be from clarified or unclarified cell lysate.

Scale-up to midi prep cannot be considered case of optimization through routine experimentation because development of this parallel, automated midi-prep procedure required a number of additional technical obstacles to be overcome. It was not possible to simply scale up the bed volume and reagent volumes used in the mini-prep because of the volume constraints imposed by the use of 1- or 1.2-mL pipette tips used with automation. The amount of plasmid requires a large amount of resin per column which is difficult to place into an automated column format. Also, the volumes of samples and solutions used to process the samples increase dramatically. Because, it was not possible to simply scale up the column bed volume and all the solution volumes proportionally. To make the invention compatible with commercial liquid handing systems and commercially-available pipette tips, a volume of 1 mL cannot be exceeded for the bed and liquid volumes in the bed.

Spin columns are not faced with this problem for scale-up. For example, a commercially-available mini-prep spin column has bed dimensions of 7.0 mm diameter and 2.05 mm height giving a bed volume of 79 $mm^3$. When the bed material is scaled up to midi-prep size, the bed dimensions increase to 13.9 mm diameter and 11.2 mm height giving a bed volume of 1700 $mm^3$. This is more than a 20 fold increase in bed size.

The bed volume used in pipette tip columns cannot be scaled up 20 fold. The bed volume of the mini-prep scale is 10-120 μL bed with the 60-80 μL bed size preferred. Certainly the bed size can be decreased if a lower recovery of plasmid is desired. But, if a larger yield of plasmid is required, it is not possible to increase the 60-80 μL bed volume 20 fold as is the

TABLE 1

Colorimetric Endotoxin Assay of Purified Plasmid DNA

|  | $A_{545}$ | [Endotoxin] (EU/mL) | [plasmid] (ng/μL) | Vol. Tested (μL) | Endotoxin (EU) | Plasmid (μg) | [Endotoxin] (EU/μg) |
| --- | --- | --- | --- | --- | --- | --- | --- |
| Spin column 1 | 0.486 | 0.17 | 183 | 100 | 0.017 | 18.3 | 0.0009 |
| Spin column 2 | 0.575 | 0.20 | 183 | 100 | 0.020 | 18.3 | 0.0011 |
| Pipette tip col. 1 | 0.526 | 0.19 | 76 | 100 | 0.019 | 7.6 | 0.0025 |
| Pipette tip col. 2 | 0.477 | 0.17 | 76 | 100 | 0.017 | 7.6 | 0.0022 |
| Pipette tip col. 3 | 0.472 | 0.17 | 76 | 100 | 0.017 | 7.6 | 0.0022 |

Scale-up to Midi-prep

Another significant point of novelty of the instant invention is in the area of scale-up. Plasmid purification protocols are typically called "mini-prep", "midi-prep" or "maxi-prep" based on their scale. Although these plasmid purification protocols are well known in the art, an automated system for performing 96 midi-preps at a time has never been described. In the instant application, scale-up to a "midi-prep" culture was achieved.

In the mini-prep embodiment, up to 20 μg of the plasmid could be recovered. For the purpose of this invention, a mini-prep automated approach is defined as a method in which the amount of plasmid or nucleic acid recovered is in the range of up to 30 μg. A scale-up to midi-prep was achieved so that 96 samples were processed simultaneously with a yield of plasmid DNA in the range of 20 to 160 μg. For a midi-prep, the yield can be in the range having a lower limit of 20, 25, or 30 μg and an upper limit of 50, 60, 80, 100, 120, 140 or 160 μg. Therefore, a midi-prep automated approach is defined as a method where the amount of plasmid or nucleic acid recovered is in the range of 20-160 μg per column. The method of case with spin column. If the pipette tip column bed volume were increased 20 fold, it would be in the range of 1.2 mL to 1.6 mL. However, when using a robotic liquid handling system in a 96-well format, pipette tips are limited to volumes of 1.0 mL or 1.2 mL at most. In practice the volume are much less than this, especially as the volume in the column taken up by the resin media. These pipette tips cannot hold enough medium for a 20-fold scale-up.

At the outset, it appeared to be impossible to scale the automated method to obtain 20-160 μg of purified plasmid because of volume constraints of the media and the solutions within the columns. In commercially-available spin or gravity-flow columns, the volumes of the solutions are increased 15 to 20 fold when scaling up from a mini-prep to a midi-prep. Clearly, this was an added difficulty when scaling an automated method performed in a 96-well format. If the resuspension, lysis and precipitation buffers were scaled up 20 fold, the total volume would be over 10 mL. Two-mL deep well plates are the most common size for the 96-well format. Four-mL deep well plates can be found, though they are not readily available. Even with 4-mL plates, multiple wells would have to be used to contain the unclarified lysate.

Growth volumes can be adjusted depending on parameters such as the richness of the growth medium and the copy number and size of the vector. In one embodiment, cells for mid-prep are grown in a flask or tube. For example, 30 mL of overnight culture is processed by a single midi-prep column. In another embodiment the starting culture is between 5-15 ml which produced approximately 50 µg of purified plasmid. With low density cultures or low copy number vectors, it may be desirable to process 30 mL of culture to get recoveries of greater than 50 µg of plasmid.

In some embodiments, growth for midi-prep is performed in multi-well plates. For instance, cells can be grown in 6-, 12-, 24-, 48- or even 96-well plates. When 96 midi-prep columns are used and growth is performed in plates having fewer than 96 wells, multiple plates are needed for growth, (e.g., four, 24-well plates can be used to grow cells for 96 midi-prep columns.) In these embodiments, the consolidation from e.g., 24-well plates to 96 columns can be performed with a liquid handing system. Alternatively, consolidation can be performed with a multi-channel or even a single-channel pipette.

Consider for example, cell growth in four 24-well plates for 96 midi-prep columns. Consolidation from the 24-well plates to 96 columns can be performed at varying stages during processing. In one embodiment, cells can be transferred directly from the 24-well plates into one or more 96-well plates. In a second embodiment, the 24-well growth plates can be centrifuged and the cell pellet can be resuspended by gentle mixing with a liquid handling robot as described previously. In this embodiment, the resuspension buffer volume can be chosen to yield the desired volume of resuspended cells. That is, a small volume of resuspension buffer can be used to produce a highly-concentrated cell suspension.

One of the first problems tackled was the size of the column bed. It preferred that the bed size not be too large because of limited chamber space above the bed. In certain embodiments, the bed volume is less than half the volume of the pipette tip in which the column is made. In these embodiments the bed volume can be less than ⅓ the volume of the pipette tip or less than ¼ of the volume. It is desirable to have considerable space above the bed so that relatively large liquid aliquots can be processed by back and forth flow.

It is also possible to use a bed volume that is greater than half the volume of the pipette tip in which the column is made. This is not preferred however for several reasons. First, a larger bed would give rise to higher resin costs. Second, a larger bed would result in a larger volume of eluted plasmid which could require further concentration, e.g., by ethanol precipitation. Third, because the resin would take up as significant portion of the column volume, it would be necessary to process smaller liquid aliquots during the capture and wash steps.

In one experiment, a 300 µL resin bed in a 1 mL pipette tip was tested. This bed height was 3.75 times higher than the mini-prep columns (80 µL resin bed) described herein. In another experiment, the column bed volume was 400 µL. Experiments were performed in which enough cell lysate was passed through the column to load the columns to capacity. Surprisingly and unexpectedly, it was discovered that the resin did have enough capacity to recover up 100 µg of plasmid. Without wishing to be bound by theory, the significant increase in plasmid yield may have been due to the porous nature of the packing material. Nevertheless the results were unexpected. The column bed size for midi-prep recovery of 20-160 µg nucleic acid recovery ranged from 85-800 µL, 200-500 µL or 300-400 µL.

The bed size can also be defined by the percentage of the pipette tip column taken up by the bed. For example, an 85 µL bed in a 1.2-mL pipette tip takes up approximately 7% of the volume available in the tip. Therefore, the bed size for a midi-prep can take up at least 7%, at least 8%, at least 12%, at least 16%, at least 20%, at least 25%, at least 29% or at least 33%, of the volume available in the tip.

Although it is the most economical to manufacture the columns from commercially-available pipette tips, it is also possible to make columns that can engage a liquid handler but are cylindrical in shape, or even another shape. In these embodiments, the resin can take up a smaller percentage of the tip.

Next, the volume constraints of the resuspension buffer, the lysis buffer, the precipitation buffer and the entire sample were examined. A smaller volume of resuspension buffer could be used with the consequence that the cell suspension would be more concentrated. A more concentrated cell suspension would give rise to a more concentrated lysate. Since the lysate is unclarified in preferred embodiments of the invention, a more concentrated lysate has more particulates, more cell debris and more genomic DNA per unit volume, making it more difficult to process.

Alternatively, a larger volume of resuspension buffer could be used and the sample could be captured from a number of wells, perhaps up to 4 or more. However, the larger volumes are more difficult to work with and would require additional disposables and expense. In one embodiment, the midi-prep procedure employs 4 mL resuspension buffer, 4 mL lysis buffer, and 6 mL of precipitation buffer, making the total volume 14 mL. A volume of 14 mL would require 8 wells of a 96-well deep-well block. So while this embodiment would be possible to automate, it is not preferred.

In order to solve this issue, several smaller resuspension, lysis and precipitation buffer volumes were tested to reduce the total volume we need to process the midi sample:

1. 300 µL Resuspension buffer, 300 µL Lysis buffer, 410 µL Precipitation buffer: total=1010 µL
2. 500 µL Resuspension buffer, 500 µL Lysis buffer, 700 µL Precipitation buffer: total=1700 µL
3. 1 mL Resuspension buffer, 1 mL Lysis buffer, 1.4 mL Precipitation buffer; total=3.4 mL
4. 2 mL Resuspension buffer, 2 mL Lysis buffer, 2.8 mL Precipitation buffer: total=6.8 mL These volumes may be adjusted to produce more concentrated reagents. However, this may produce more particulate or the salts and buffers making up the reagents may become insoluble at the concentrations required by the process. A range of reagent concentrations up to, and including those concentrations listed in the table below can be used in the automated midi-prep procedure. In some embodiments, more concentrated neutralization reagents can be used by performing the neutralization in two steps. That is, the guanidine hydrochloride could be added prior to the potassium acetate or vice versa. In certain embodiments, these reagent concentrations can be used in the automated mini-prep procedure.

| Buffer Name | Content |
| --- | --- |
| Resuspension buffer | 1M Tris-HCl pH 8.0, 1M EDTA, 4 mg/mL RNase A |
| Lysis buffer | 6M NaOH, 10% SDS |
| Neutralization buffer | 10M guanidine hydrochloride 5M Potassium acetate pH 4.5 |
| Wash buffer | 1M TRIS-HCl pH 7.5, and up to 100% Ethanol |

In some embodiments, the ratio of Resuspension buffer to Lysis buffer to Precipitation buffer is considered. This ratio can be 1:1:1.2. In certain embodiments, less Resuspension buffer is used in order to minimize the total volume. That is, the ratio of Resuspension buffer to Lysis buffer can be 1:1 or it can be less. For example, 150 μl of Resuspension buffer can be used with 500 μl Lysis buffer. When this small volume of resuspension buffer is used, the buffer can be 10-fold more concentrated. Alternatively, 300 μl or 500 μl Resuspension buffer can be used with 500 μl Lysis buffer.

In certain embodiments, the resuspended cells can be transferred to a 96-well plate for further processing. However, it is also possible to continue processing in the 24-well format. Cell lysis and precipitation can be performed in the 24-well format, and the aqueous portion of the resulting unclarified lysate can be processed on a midi-prep column.

In preferred embodiments, the vector is captured by repeated aspiration and expulsion through the open lower end of the midi-prep column. In other embodiments, the sample can be applied to the open upper end of the midi column and allowed to pass through the column by vacuum or gravity flow.

When capture is performed by repeated aspiration and expulsion, partial sampling of the unclarified lysate can be used as described above. In one embodiment, partial sampling can be performed in several aliquots. After each aliquot is processed, it can be expelled to waste.

As with the mini-prep, the wash and elution steps can be done with aspiration and expulsion or they can be done by using by gravity flow. This is the first known automated method that produces plasmid DNA at the midi-prep scale of up to about 160 μg of plasmid DNA. The 96-well automated method can be performed with clarified or unclarified lysates.

The Columns

In the subject invention, a bed of medium is contained in a column, wherein the bed is held in place with a bottom frit. In some embodiments, the columns are additionally comprised of a top frit. Non-limiting examples of suitable columns, particularly low dead volume columns are presented in U.S. Pat. No. 7,482,169. It is to be understood that the subject invention is not limited to the use of low dead volume columns. The columns may be configured into plates or racks or used individually.

Typically, the column is comprised of a column body having an open upper end, an open lower end, and an open channel between the upper and lower ends of the column body; a bottom frit extending across the open lower end and a bed of medium positioned inside the open channel above the bottom frit.

FIG. 1 depicts an embodiment of pipette tip column construction. Disposable pipette tip 160 is cut approximately ¼ inch from the lower end and frit 174 is welded to the lower end of the tip body. A silica resin 184 was then transferred into the tip. In certain embodiments, upper frit 198 is placed above the resin, e.g., using a friction fit. The lower end is removed from a second pipette tip 190 and the remaining upper end is inserted into pipette tip 160 and held in place by a friction fit. Pipette tip 190 is specific for the liquid handling system that will be used to process the columns. In some embodiments, pipette tip 190 is additionally comprised of barrier 182. In other embodiments, barrier 182 is absent. Barrier 182 is particularly useful when frit 198 is absent because it serves to confine resin 184 within the pipette tip column during shipping.

The columns will have some backpressure due to the bed of medium and the frit(s). The backpressure of a column will depend on the average bead size, bead size distribution, average bed length, average cross sectional area of the bed, backpressure due to the frit and the viscosity and flow rate of the liquid passing through the bed. For a column described in this application, the backpressure at 2 mL/min flow rate ranged from 0.01 to 5 psi, and more commonly 0.05 and 2 psi.

Media

Because the invention is directed to the purification and/or concentration of nucleic acids, extraction surfaces capable of adsorbing such molecules are particularly relevant. The chemistry employed in the present invention is typically based on normal phase or ion-exchange. Ion-pairing may also be used for nucleic acid purification. In general, these chemistries, methods of their use, appropriate solvents, etc. are well known in the art.

The media used in the column is preferably a form of water-insoluble particle (e.g., a porous or non-porous bead, fiber or other particle) that has an affinity for the nucleic acid of interest. Silica beads are suitable for the columns of the invention. Chromosorb P is large and works well. Silicon quartz also works well. Other suitable materials include celite, diatomaceous earth, silica gel, silica gel, (Davisil, Impaq, Biotage), metal oxides and mixed metal oxides, glass, alumina, zeolites, titanium dioxide, zirconium dioxide. Ion exchangers made of inorganic or polymeric substrates also work quite well.

The bed volume of the medium used in the columns of the invention is typically in the range of 10 μL and 500 μL, 10 μL and 300 μL, 20 μL and 100 μL, or between about 15 μL and 80 μL. For midi-prep scale the bed volume of the medium used in the columns of the invention is typically in the range of 100 μL and 800 μL, 100 μL and 300 μL, 200 μL and 300 μL, or between about 200 μL and 400 μL.

The average particle diameters of beads of the invention are typically in the range of about 20 μm to several hundred micrometers, e.g., diameters in ranges having lower limits of 20 μm, 30 μm, 40 μm, 50 μm, 60 μm, 70 μm, 80 μm, 90 μm, 100 μm, 150 μm, 200 μm, 300 μm, or 500 μm, and upper limits of 30 μm, 40 μm, 50 μm, 60 μm, 70 μm, 80 μm, 90 μm, 100 μm, 150 μm, 200 μm, 300 μm, 500 μm, 750 μm, or 1 mm.

The space between resin particles can also be important. This space increases with looser packing of the column. Preferred beds are not tightly packed.

Frits

One or more frits is used to contain the bed of medium in a column. Frits can take a variety of forms, and can be constructed from a variety of materials. The frits of the invention are porous, since it is necessary for fluid to be able to pass through the frit. The frit should have sufficient structural strength and integrity to contain the extraction media in the column. It is desirable that the frit have little or no affinity for chemicals with which it will come into contact during the extraction process, particularly the analyte of interest. Frits of various pores sizes and pore densities may be used provided the free flow of liquid and particulates is possible. Frits of pore size large enough to prevent plugging from cell debris are of particular interest.

In one embodiment, a single frit (e.g., a lower, or bottom, frit) extends across the open channel of the column body. Preferably, the bottom frit is attached at or near the open lower end of the column, e.g., extending across the open lower end. Normally, a bed of medium is positioned inside the open channel in contact with the bottom frit.

In some preferred embodiments of the invention, the bottom frit is located at the open lower end of the column body. This configuration is not required, i.e., in some embodiments, the bottom frit is located at some distance up the column body from the open lower end. Some frits of the invention have a large pore size frit.

In certain embodiments, a top frit may be employed. For example, in some embodiments, a second frit extends across the open channel between the bottom frit and the open upper end of the column body. In this embodiment, the top frit, bottom frit and column body (i.e., the inner surface of the channel) define a media chamber wherein a bed of medium is positioned. The frits should be securely attached to the column body and extend across the column body to completely occlude the channel, thereby substantially confining the bed of medium inside the media chamber.

In some embodiments, the top frit can be just above the bed of medium or in contact with the bed of medium. In other embodiments, the top frit is positioned well above the medium, e.g., 25 mm or more above the medium in a 200 μl pipette tip column or 50 or more mm above the bed in a 1.2-mL pipette-tip column. The position of the top frit can be proximal to open upper end of the pipette tip column. That is, the top frit can be closer to the open upper end of the column than to the bed medium. In these embodiments, the bed is not packed and the medium can occupy well under 50% of the volume of the extraction media chamber and the top frit can be significantly thicker than the bottom frit. In some embodiments, liquids may not flow through the top frit.

The position of the top frit over the bed may just touch the top of the resin bed or be positioned substantially above the resin bed. When the frit is above the resin bed, the resin bed may move or expand with aspiration of liquids including the sample containing the particulates. The bed may move down against the bottom frit with expulsion of the liquid.

The performance of the column is typically enhanced by the use of frits having pore or mesh openings sufficiently large to allow cell debris or other particulates to flow through the frit without clogging or plugging under low pressures applied by a pipette or liquid handler. Of course, the pore or mesh openings of course should not be so large that they are unable to adequately contain the extraction media in the chamber. Frits of the invention preferably have pore openings or mesh openings of a size in the range of about 5-500 μm, more preferably 10-200 μm, and still more preferably 100-150 μm, e.g., about 120 μm.

In some cases, it is necessary to consider the relationship between the frit pore size and the particle diameter. Specifically, it is possible to increase the frit pore size when the particle diameter is increased. For example, a frit pore size of 100 μm was used successfully with a range of different resins.

Some embodiments of the invention employ a thin frit, preferably less than 2000 μm in thickness (e.g., in the range of 20-2000 μm, 40-350 μm, or 50-350 μm), more preferably less than 200 μm in thickness (e.g., in the range of 20-200 μm, 40-200 μm, or 50-200 μm), more preferably less than 100 μm in thickness (e.g., in the range of 20-100 μm, 40-100 μm, or 50-100 μm). However, thicker frits, up to several mm, 5 and even 10 mm, thick may be used if the pore size of the frit can be increased dramatically. Some preferred embodiments of the invention employ a membrane screen as the frit. The use of membrane screens as described herein typically provide this low resistance to flow and hence better flow rates, reduced backpressure and minimal distortion of the medium. The membrane can be a woven or non-woven mesh of fibers that may be a mesh weave, a random orientated mat of fibers i.e. a "polymer paper," a spunbonded mesh, an etched or "pore drilled" paper or membrane such as nuclear track etched membrane or an electrolytic mesh (see, e.g., U.S. Pat. No. 5,556,598). The membrane may be, e.g., polymer, glass, or metal provided the membrane is low dead volume, allows movement of the sample and various processing liquids through the column bed, may be attached to the column body, is strong enough to withstand the bed packing process, is strong enough to hold the column bed of beads, and does not interfere with the extraction process i.e. does not adsorb or denature the sample molecules.

The frit can be attached to the column body by any means which results in a stable attachment. For example, the screen can be bonded to the column body through welding or gluing. The column body can be welded to the frit by melting the body into the frit, or melting the frit into the body, or both. Alternatively, a frit can be attached by a friction fit or by means of an annular pip, as described in U.S. Pat. No. 5,833,927.

The frits of the invention can be made from any material that has the required physical properties described herein. Examples of suitable materials include polymer, sintered polymer, fiber, nylon, polyester, polyamide, polycarbonate, cellulose, polyethylene, nitrocellulose, cellulose acetate, polyvinylidine difluoride, polytetrafluoroethylene (PTFE), polypropylene, polysulfone, PEEK, PVC, vinyl polymer, metal (e.g., steel), ceramic and glass.

In certain embodiments of the invention, a wad of fibrous material is included in the column, which extends across the open channel below the open upper end of the column body, wherein the wad of fibrous material and open channel define a media chamber, wherein the medium is positioned within the media chamber. This wad of fiber can be a porous material of glass, polymer, metal, or other material having large pores. In some embodiments, the wad of fibrous material is used in lieu of an upper frit.

Solvents

Disruption of bacterial cell membranes is typically accomplished using an alkaline solution containing a detergent. Any detergent that effectively disrupts the cell membrane can be used for this purpose. In other embodiments, the lysis procedure is mechanical or physical. In some methods, the lysis procedure involves treatment with a surfactant.

The lysis procedure is usually followed by the addition of a neutralizing solution. The neutralization solution may contain an acid. It may also contain a chaotropic agent and/or other components.

In certain embodiments of the invention, chaotropic agents can be added to the sample prior to plasmid capture. Examples of chaotropic reagents include sodium iodide, sodium perchlorate, guanidine thiocyanate (GuSCN), urea, guanidine hydrochloride (GuHCl), potassium iodide, sodium perchlorate, potassium chloride, lithium chloride, sodium chloride, urea or mixtures of such substances.

Examples of suitable solvents for use with the invention are shown in Tables 2 and 3.

TABLE 2

| | Normal Phase Extraction | Normal Phase Chaotropic Extraction | Reverse Phase Ion-Pair Extraction |
| --- | --- | --- | --- |
| Typical solvent polarity range | Low to medium | High to medium | High to medium |
| Typical sample loading solvent | Hexane, toluene, $CH_2Cl_2$ | chaotropic buffers alcohol | $H_2O$, buffers, ion-pairing reagent |
| Typical desorption solvent | Ethyl acetate, acetone, $CH_3CN$ (Acetone, acetonitrile, isopropanol, methanol, water, | $H_2O$/buffer | $H_2O/CH_3OH$, ion-pairing reagent $H_2O/CH_3CN$, ion-pairing reagent (Methanol, chloroform, acidic |

TABLE 2-continued

|  | Normal Phase Extraction | Normal Phase Chaotropic Extraction | Reverse Phase Ion-Pair Extraction |
|---|---|---|---|
|  | buffers) |  | methanol, basic methanol, tetrahydrofuran, acetonitrile, acetone, ethyl acetate) |
| Sample elution selectivity | Least polar sample components first | Most polar sample components first | Most polar sample components first |
| Solvent change required to desorb | Increase solvent polarity | Decrease chaotropic buffer | Decrease solvent polarity |

TABLE 3

| Desorption Solvent Features | Ion Exchange Extraction | Hydrophobic Interaction Extraction | Affinity Phase Extraction |
|---|---|---|---|
| Typical solvent polarity range | High | High | High |
| Typical sample loading solvent | $H_2O$, buffers | $H_2O$, high salt | $H_2O$, buffers |
| Typical desorption solvent | Buffers, salt solutions | $H_2O$, low salt | $H_2O$, buffers, pH, competing reagents, heat, solvent polarity |
| Sample elution selectivity | Sample components most weakly ionized first | Sample components most polar first | Non-binding, low-binding, high-binding |
| Solvent change required to desorb | Increase ionic strength or increase retained compounds pH or decrease pH | Decrease ionic strength | Change pH, add competing reagent, change solvent polarity, increase heat |

Methods for Using the Columns

The method involves capturing nucleic acids on pipette tip columns. The method can be performed in parallel and can be automated. Prior to the capture step, the columns are usually wetted with an equilibration solution. After capture, the columns are washed to remove non-specifically bound material. Then the nucleic acids are released from the column in an elution step. In certain embodiments of the method, the sample, wash and or desorption solvents are aspirated and discharged from the column more than once, i.e., a plurality of in/out cycles are employed to pass the solvent back and forth through the bed more than once.

The invention provides a pipettor (such as a multi-channel pipettor) suitable for acting as the pump in methods such as those described herein. In some embodiments, the pipettor comprises an electrically driven actuator. The electrically driven actuator can be controlled by a microprocessor, e.g., a programmable microprocessor. In various embodiments the microprocessor can be either internal or external to the pipettor body.

In preferred embodiments of the invention, a plurality of columns is operated in a parallel fashion, e.g., multiplexed. Multiplexing can be accomplished, for example, by arranging the columns in parallel so that fluid can be passed through them concurrently. When a pump is used to manipulate fluids through the column, each column in the multiplex array can have its own pump, e.g., syringe pumps activated by a common actuator. Alternatively, columns can be connected to a common pump, a common vacuum device, or the like.

In certain embodiments the pipettor is a multi-channel pipettor. In other embodiments, a robotic system such as those commercially available from Zymark, Hamilton, Beckman, Tecan, Packard, Matrix, PhyNexus, Agilent and others are used for plasmid purification. Those robots having a 96-channel pipetting head are particularly preferred.

In some embodiments, throughput is maximized by performing some steps with bidirectional flow and other steps by vacuum, pressure or gravity flow. For example, the capture step can be performed using bidirectional flow and the wash and elution steps can be performed using vacuum or gravity flow. In these embodiments, the pipetting head of the robotic liquid handler can be utilized more efficiently for simply dispensing liquids, allowing a greater number of columns to be processed in parallel. It is also possible to perform the capture, wash and elution steps using gravity or vacuum.

The invention also provides software for implementing the methods of the invention. For example, the software can be programmed to control manipulation of solutions and addressing of columns into sample vials, collection vials, for spotting or introduction into some device for further processing.

Wide bore pipette tips can be used for adding the Lysis buffer and Precipitation when making the unclarified lysate. Wide bore pipette tips are known in the art and commercially available. Slow flow rates, e.g., 1 ml/min can also be used when preparing the clarified lysate.

During aspiration and expulsion, the lower end of the pipette tip column can be positioned relatively close to the corresponding well bottom, e.g., within a range having a lower limit of about 0.05 mm, 0.1 mm, 0.2 mm, 0.3 mm, 0.4 m, 0.5 mm, 1 mm, 2 mm, 3 mm, 4 mm, or 5 mm from the bottom of the well, and an upper limit of 0.3 mm, 0.4 m, 0.5 mm, 1 mm, 2 mm, 3 mm, 4 mm, 5 mm, 6 mm, 7 mm, 8 mm, 9 mm or 10 mm of the well bottom. For example, in some embodiments the open lower end of a pipette tip column is positioned with between 0.05 and 2 mm from a well bottom, or between 0.1 and 1 mm from a well bottom. The term "well bottom" does not necessarily refer to the absolute bottom of a well, but to the point where the tip makes contact with the well when the tip is lowered to its full extent into the well, i.e., a point where the tip can seal with the well surface. For example, in some microwell plate formats the wells taper down to an inverted conical shape, so a typical tip column will not be able to make contact with the absolute bottom of the well.

The invention also includes kits comprising one or more reagents and/or articles for use in a process relating to solid-phase extraction, e.g., buffers, standards, solutions, columns, sample containers, etc.

Purification of Plasmid DNA from *E. Coli*

Nucleic acids and particularly plasmids can be purified from any source including eukaryotic or prokaryotic cells, tissues, body fluids (blood, serum, plasma, saliva, urine, feces), tissue culture, bacteria, viruses. The purification procedure can be used with low, medium or high copy number plasmids. The instant invention can also be used to isolate nucleic acids from a gel.

When purifying plasmid DNA from *E. coli*, the first step is cell growth. A person of skill in the art can select the appropriate growth conditions depending on the cell type, number of samples, desired yield, etc. For example, bacterial cells can be grown at 37° C. in a 96-well deep-well block with shaking at 300 rpm and harvested in the late logarithmic stage of growth. The deep-well block can be selected according to the desired culture volume. For example, a 4-ml deep well block can be used if a larger cell culture is required. Alternatively, cells can be grown in tubes or flasks if a larger volume is required. Generally, a rich medium is used such as Terrific Broth, 2xYT or Agencourt Ale (Beckman Coulter) containing the appropriate antibiotic. After the cells are grown, they are centrifuged and the growth medium is discarded.

The next step involves resuspension of the cells e.g., in a buffer. From this point, the remainder of the procedure can be fully automated with the use of a liquid handling system. In those embodiments in which the procedure is automated, a resuspension buffer is added and the cell suspension is repeatedly aspirated and expelled from a pipette tip until the cells are completely resuspended. Alternatively, the resuspension step may be performed manually by vortexing until the cell pellet is fully resuspended.

After resuspension, the next step is cell lysis. Lysis can be accomplished by a number of means including physical or chemical action. Non-limiting examples of lysis methods include mechanical, such as ultrasonic waves, mortar and pestle, osmotic shock, chemical e.g. by means of detergents and/or chaotropic agents and/or organic solvents (e.g. phenol, chloroform, ether), heat and alkali. Lysis via chemical means can be performed on a liquid handling system by addition of a lysis solution to the resuspended cells.

A precipitation buffer is added to the lysed cell suspension to precipitate the genomic DNA prior to capture. In preferred embodiments, the precipitation buffer is comprised of chaotropic salts.

Typically, gentle mixing with a wide-bore pipette tip and a relatively low flow rate is used at this step. After lysis, the plasmid is captured using a pipette tip column. In existing methods, a centrifugation step is usually performed following cell lysis to pellet cell debris. However, an advantage of the instant invention is that this centrifugation step can be bypassed in preferred embodiments, making the method considerably more automated than other methods. In alternate embodiments, the sample can be centrifuged to produce a clarified lysate which is captured on the pipette tip column.

The column can be equilibrated with water or buffer prior to the capture step. Equilibration can be performed by a single aspiration and expulsion of water or buffer from the column. After the pipette tip columns are equilibrated, the plasmid can be captured on the equilibrated column by repeated aspiration and expulsion. In alternate embodiments, the sample is captured using gravity flow.

After capture, the plasmids bound to the column are usually washed to remove non-specifically bound materials. One or more wash steps can be performed. When more than one wash is performed, the same wash solution can be used for multiple washes or different wash solutions can be used. In certain embodiments, the wash solution contains an organic solvent, e.g., alcohol.

Wash steps can be performed with back and forth flow or unidirectional flow using gravity or vacuum. The advantage of performing the wash steps by unidirectional flow is that higher throughput can be achieved. That is, when plasmid purification is performed on a liquid handling robot, throughput can be increased by utilizing the liquid handling head simply for dispensing wash solution to multiple plates. When the wash is performed by back-and-forth flow, the liquid handling head can process only one plate at a time.

After the wash step, air is passed through the columns to remove any organic solvent remaining from the wash step. This can be accomplished by depositing the pipette tip columns onto a vacuum block and drawing air through the columns with a vacuum. A vacuum block adaptor was custom built for this process and is described in more detail below.

In certain embodiments, air is passed through the columns long enough to remove the organic solvent present in the wash solution, but not long enough to dry the columns completely.

In other embodiments, the columns can be dried completely. When the residual organic solvent is measured, it is in the range of less than 10%, less than 9%, less than 8%, less than 7%, less than 6%, less than 5%, less than 4%, less than 3%, less than 2% or less than 1%.

In other embodiments, air is passed through the columns with positive pressure. Alternatively, it is possible to dry or remove the ethanol or other organic solvent after elution by methods such as speed-vac, air drying, heating or applying a gas stream to the wells containing the eluted sample.

The elution of plasmid from the column can be accomplished with back and forth flow or unidirectional flow. Generally elution volumes are in the range of about 1-5 times the bed volume. When back-and-forth flow is used, air can be aspirated into the pipette tip column prior to aspirating the elution buffer. This air can be used after expulsion of the plasmid to ensure complete expulsion of all the liquid in the column.

Generally, the elution buffer is aqueous and has a pH between 6 and 10. In some embodiments, the column is incubated with the elution buffer for a period of time. In these embodiments, the column and elution buffer are incubated for at least 1 minute, at least 2 minutes, at least 3 minutes, at least 4 minutes, at least 5 minutes, at least 10 minutes or at least 15 minutes. In other embodiments, the incubation step is omitted.

After the incubation step, the purified plasmid is expelled from the pipette tip column. To ensure the maximum volume of purified plasmid is recovered, a blow-out step can be performed by expelling the air aspirated as described above.

The concentration of plasmid DNA purified by this method is generally at least 50 ng/uL, at least 75 ng/uL, at least 100 ng/uL or greater and an $A_{260/280}$ ratio of 1.8-2.0. Most importantly, the plasmid DNA purified by these methods is high quality, free of endotoxin and can be used for any downstream application including sequencing, transfection and transformation.

The entire process from cell harvest to eluted plasmid DNA generally takes about 1 hour. However in some embodiments, the entire procedure can be performed in the range of 30 to 90 minutes or between 45 and 75 minutes.

The Vacuum Block Adapter

Existing commercially-available vacuum DNA preparation methods utilize manifolds that are designed only to pull liquid through columns or plates. Common formats for these manifolds are 24-column and 96-column capacity. With these manifolds, it is sometimes necessary to monitor liquid flow through the different columns to ensure the liquid has passed through all the columns.

Figure 2:
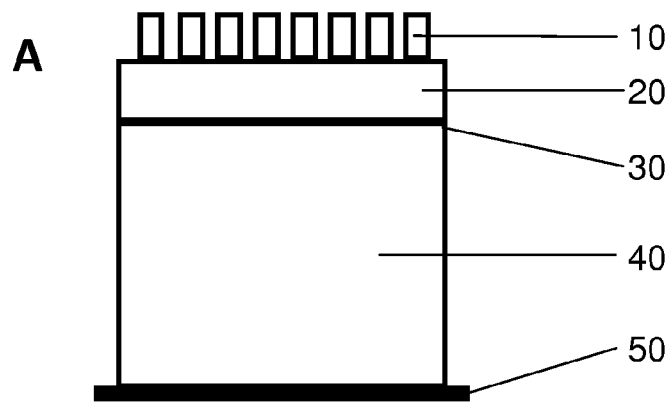
FIG. 2 depicts an embodiment of the vacuum block adapter with front and side views.
Figure 2:
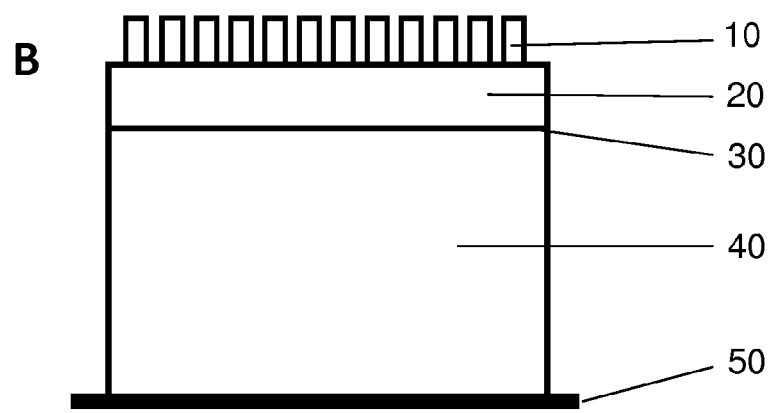
Figure 2:
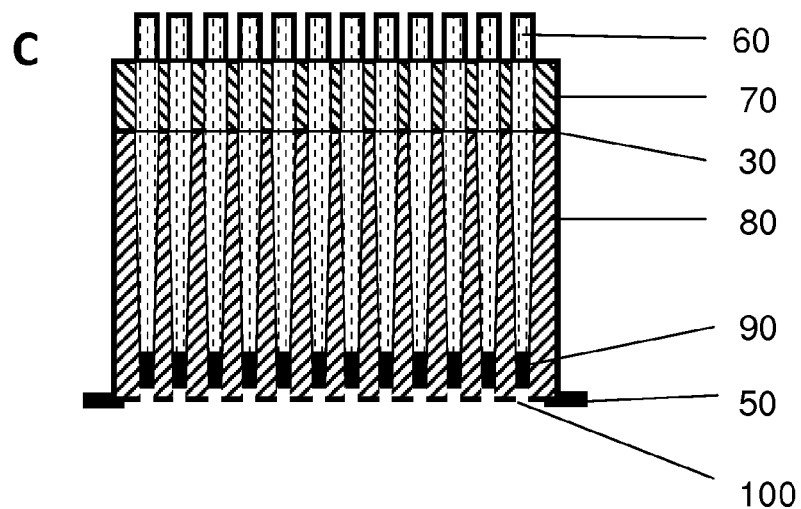
Figure 3:
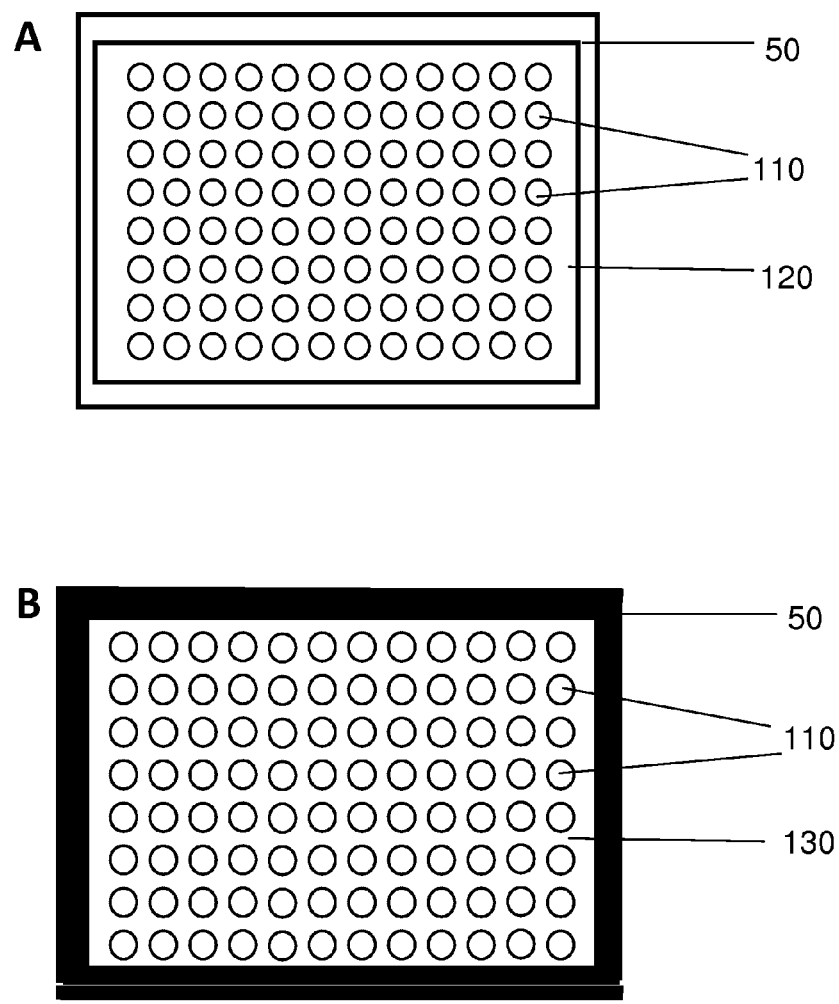
FIG. 3 depicts an embodiment of the vacuum block adapter with top and bottom views.

One embodiment of the vacuum adapter block is shown in FIGS. 2 and 3. In contrast to existing manifolds, the channels within the block completely surround each column over substantially the entire length of the column. With this design, liquid and air flow is comparable between columns.

In other embodiments, the vacuum block adaptor could be designed with a channel that surrounds each column but not over the entire length to seal with the pipette tip column, primarily at the lower end of the column.

In some embodiments, vacuum applied to the manifold can be controlled by software to apply vacuum to the columns at the appropriate time for the appropriate duration.

FIG. 2 depicts embodiments of the side and front views of the vacuum adapter block and FIG. 3 shows the top and bottom of the block. In this embodiment, the block contains positions for 96 columns. In other embodiments, the block may contain positions for any number of columns including 6, 8, 12, 24, 48 or 384 columns.

FIG. 2A depicts an embodiment of the side view of the adapter block, the tops of eight columns 10 are inserted into top block 20. Top block 20 is separated from bottom block 40 by sealing gasket 30. The gasket serves to seal around each individual column when they are inserted into the block so that the vacuum is applied through the columns and not around the sides of the column bodies. The bottom of bottom block 40 contains plastic lip 50. In this embodiment, the lip conforms to SBS standardized format for 96-well plates so that the base of the block can be inserted into the vacuum manifold or any deck position of a robotic liquid handler.

FIG. 2B depicts the front view of the vacuum adapter block pictured in FIG. 2A. It is identical to the side view shown in view A except that the row of twelve columns 10 can be seen.

FIG. 2C is a cut-away view of the vacuum block adapter front view. Pipette tip columns 60 are exposed to show that when inserted into the block they extend almost to the bottom. In this embodiment, the end of the column does reach the bottom of the vacuum block. In other embodiments, the lower ends of the columns will be even with the bottom of the vacuum block. In still other embodiments, the ends of the columns will extend out past the base of the vacuum block. Opening 100 allows the vacuum to be applied at the bottom of the block and allows liquid and air passage through the columns sealed by gasket 30. Cross section of top block 70 is separated from cross section of bottom block 80 by gasket 30. In certain embodiments, the column shape is frustoconical and the holes at the interface of top block 70 and bottom block 80 have a smaller diameter than those on the upper surface of top block 70. The plasmid is captured from the sample by column packing material 90, and then washed and eluted.

FIG. 3 depicts and embodiment of the top view of the vacuum adapter block and FIG. 3B shows the bottom view of the vacuum block. Lip 50 lies at the bottom of the block near bottom surface 130. Pipette tip columns are inserted into through holes 110 from top surface 120.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Evaluation of an 80 µL Bed Volume Pipette Tip Column Containing a Resin for Purification of Plasmid from Eukaryotic Cells In this example, the performance of 80 µL bed volume pipette tip columns is evaluated. The pipette tip column was constructed from a 200 µL pipette tip (Tecan) and is packed with a silica-based particle resin. These columns, buffer conditions and column processing procedures are tested for the recovery of plasmid DNA from yeast. The yield and quality are assessed by UV spectrometry and agarose gel electrophoresis.

Samples are prepared by growing a single yeast colony in 25 mL medium supplemented with the appropriate carbon source to propagate the DNA vector. The liquid culture is incubated at 30° C. with shaking until the culture becomes turbid. The culture is divided into equal aliquots and subjected to centrifugation at 5,000×g for 15 minutes to pellet the yeast. The supernatant is discarded and the pellets are lysed by mortar and pestle, using liquid nitrogen and resuspended in buffer.

To purify the plasmid DNA from the lysed yeast cells, the pipette tip columns are processed by the ME semi-automated purification system (PhyNexus, Inc., San Jose, Calif.). The columns are equilibrated with 200 µL 7M guanidinium-HCl by performing one cycle of back-and-forth flow at 500 µL/min and a 20 second pause at the end of the aspirate and dispense steps.

The yeast lysate is subjected to pipette tip column processing for capture of the plasmid DNA by using at least 24 back-and-forth cycles at a flow rate of 250 µL/min with 20 second pauses after the end of each aspirate and dispense step.

Following plasmid capture on the pipette tip column, the columns are washed with 200 µL wash 1 buffer consisting of 10 mM Tris-HCl pH 6.6, 5M guanidinium-HCl and 30% ethanol. This is followed by a second wash in wash 2 buffer consisting of 10 mM Tris-HCl pH 7.5 and 80% ethanol. Both wash procedures are carried out using one cycle of back-and-forth flow at a flow rate of 500 µL/min with 20 second pauses at the end of each aspirate and expel step. A blow out step is incorporated to remove all residual wash buffer from the resin bed.

DNA plasmid is released from the column with 300 µL elution buffer consisting of water. The procedure to release the DNA is 8 back-and-forth cycles at a flow rate of 250 µL/min with 20 second pauses after the end of each aspirate and dispense step.

Example 2

Purification of Plasmid DNA from *E. Coli*

Columns and methods for purifying plasmid DNA from *E. coli* lysate were developed for 96 samples at a time. The columns used in this example were 80 µL bed columns fitted with 100 µm pore size screen bottom frits. The method was designed to operate on a Tecan EVO, Biomek FX or other robotic liquid handler. The solutions used are listed in Table 4.

*E. coli* cells were grown to late logarithmic phase, harvested by centrifugation and then resuspended in buffer. The plasmid purification procedure developed was as follows.
1. Add 250 µL of Lysis buffer to resuspended cells using gentle pipette mixing for 3 minutes.
2. Add 350 µL of Neutralization buffer to lysed culture using gentle pipette mixing for 3 minutes.
3. Attach plasmid DNA pipette tip columns to 96 channel head.
4. Equilibrate the pipette tip columns by cycling through the equilibration buffer.
   Use 2 cycles at 0.5 mL/min flow rate.
5. Capture the plasmid DNA.
   Use 24 cycles at 0.25 mL/min flow rate.
6. Wash (Wash1 buffer, 500 µL) the captured plasmid DNA.
   Use 2 cycles at 0.5 µL/min flow rate.
7. Wash (Wash2 buffer, 500 µL) the captured plasmid DNA.
   Use 2 cycles at 0.5 µL/min flow rate.

8. Wash (Wash2 buffer, 500 μL) the captured plasmid DNA.
   Use 2 cycles at 0.5 mL/min flow rate.
9. Blowout remaining wash buffer.
10. Elute the captured plasmid DNA.
    Use 16 cycles at 0.25 mL/min flow rate.

The yield was approximately 5 μg per well. The purity was examined with agarose gel electrophoresis and UV absorption with $A_{260}/A_{280}$ ratio between 1.8 and 2.0.

Example 3

Purification of Plasmid DNA from *E. Coli* Pellets

Columns and methods for purifying plasmid DNA from *E. coli* lysate were developed for 96 samples at a time. The columns used in this example were 80 μL bed columns fitted with 100 μm pore size screen bottom frits. The method was designed to operate on a Tecan EVO, Biomek FX or other robotic liquid handler.

*E. coli* cells were grown to late logarithmic phase, harvested by centrifugation and then resuspended in 150 μL Resuspension Buffer (50 mM Tris-HCl pH 8.0, 10 mM EDTA, 400 μg/mL RNase A). The plasmid purification procedure was performed as follows.

Using wide bore pipette tips, 150 μL of Lysis buffer (200 mM NaOH, 1% SDS) was added to the resuspended cells using gentle pipette mixing. Next, the precipitation step was carried out by the addition of 210 μL of Precipitation Buffer (0.9 M potassium acetate pH 4.8, 4.2 M guanidinium hydrochloride) to lysed cells using gentle pipette mixing. The wide bore pipette tips were discarded and the liquid handling robot attached plasmid DNA pipette tip columns to the 96-channel head. The pipette tip columns were equilibrated in 500 μL of water with back-and-forth cycling of the equilibration buffer. A typical cycle consists of aspiration of 180 μL at a flow rate of 0.5 mL/minute followed by a pause of about 30 seconds while maintaining the end of the plasmid DNA pipette tip columns at the bottom of the well of a deep well or microplate. The second half of a cycle consists of dispense of 180 μL at a flow rate of 0.5 mL/minute followed by a pause of about 30 seconds while maintaining the end of the plasmid DNA pipette tip columns at the bottom of the well of a deep well or microplate. The plasmid DNA pipette tip columns next capture plasmid from the prepared *E. coli* samples using 14 cycles at 0.25 mL/min flow rate with 20 second pauses. After plasmid capture, the plasmid DNA pipette tip columns were blotted onto absorbent lab paper by to remove cell debris and precipitants. The DNA pipette tip columns next went through wash by submerging the end of the column on 500 μL of Wash Buffer (100 mM Tris-HCl pH 7.5, 65% ethanol) using 2 cycles at 0.5 μL/min flow rate and 20 second pauses. Wash was repeated twice in 500 μL of fresh Wash Buffer. The ethanol was dried from the resin bed by ejecting the plasmid DNA pipette tip columns in a vacuum adapter and a vacuum was applied that was capable of moving at least 4 Cubic Feet per Minute (CFM). The vacuum was applied for 5 minutes. The liquid handling robot reattached the plasmid DNA pipette tip columns and eluted the pure plasmid DNA by aspirating 170 μL Elution Buffer (10 mM Tris-HCl pH 8.5) and incubating it for 5 minutes. The plasmid was released by dispensing 170 μL into a microplate.

Example 4

Comparison of Pipette Tip Columns and Spin Columns

The pipette tip columns used in this example contained 80 μL of Chromosorb P resin (Sigma Aldrich) and were fitted with 105 μm pore size screen bottom frits. A side by side comparison with commercial spin columns was made using buffers listed in Table 4. *E. coli* was grown overnight in 1.4 mL medium in a 96-well deep-well plate. The results of three representative samples are shown in Table 5.

TABLE 4

| Buffers | |
|---|---|
| Buffer Name | Content |
| Resuspension buffer | 50 mM Tris-HCl pH 8.0, 10 mM EDTA, 100 ug/mL RNase A |
| Lysis buffer | 200 mM NaOH, 1% SDS |
| Neutralization buffer | 4.2M guanidine hydrochloride 0.9M Potassium acetate pH 4.5 |
| Equilibration buffer | water |
| Wash1 buffer | 5M guanidine hydrochloride 30% Ethanol, 10 mM TRIS-HCl pH 6.6 |
| Wash2 buffer | 10 mM TRIS-HCl pH 7.5, 80% Ethanol |
| Elution buffer | Water |

TABLE 5

Comparison of pipette tip columns and spin columns

| Column Name | A260 | Conc (ng/μL) | A260/ A280 | Total μg | Combined total μg |
|---|---|---|---|---|---|
| Spin C1 (100 μL elution) | 0.86 | 43.05 | 1.78 | 4.30 | |
| Spin C2 (100 μL elution) | 0.19 | 9.6 | 1.63 | 0.96 | |
| Spin C3 (100 μL elution) | 0.14 | 7.05 | 1.10 | 0.70 | 5.97 |
| Pipette Tip [top frit] E1 (100 μL) | 1.12 | 56.2 | 1.97 | 5.62 | |
| Pipette Tip [top frit] E2 (100 μL) | 0.51 | 25.5 | 1.93 | 2.55 | |
| Pipette Tip [top frit] E3 (100 μL) | 0.28 | 14.25 | 1.73 | 1.42 | 9.59 |
| Pipette Tip [no top frit] E1 (100 μL) | 0.61 | 30.75 | 1.92 | 3.07 | |
| Pipette Tip [no top frit] E2 (100 μL) | 0.64 | 31.95 | 1.92 | 3.19 | |
| Pipette Tip no [top frit] E3 (100 μL) | 0.37 | 18.55 | 1.80 | 1.85 | 8.12 |

Representative results from purification of plasmid performed with a commercial spin columns used with three sequential elutions (Spin C1, Spin C2 and Spin C3) and two types of pipette tip columns. E1, E2 and E3 refer to the recovery from three sequential elution aliquots, elutions 1 through 3.

Example 5

Mini-prep of *E. Coli* Plasmid DNA from 96 Samples at a Time

Figure 4:
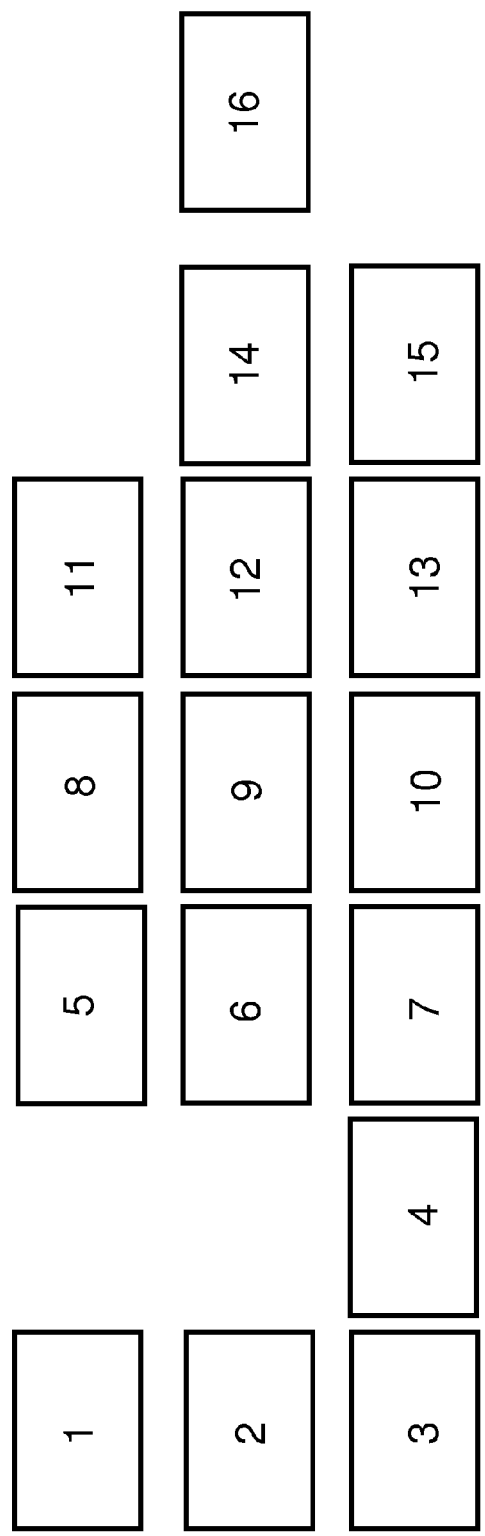
FIG. 4 depicts the layout of the deck of the Tecan Freedom Evo automated liquid handler.

Single colonies were inoculated into 1.4 ml rich medium (containing the appropriate antibiotic) in a 2-ml deep-well block and incubated at 37° C. and 300 rpm for 16 hours. The deep-well block was centrifuged and the medium was discarded. The plate was then transferred to a Tecan Freedom Evo liquid handler with the deck set up described as follows and shown in FIG. 4.

Positions 1 through 3 contain boxes of 200-μL pipette tips. Position 4 has a box of 96 pipette tip columns. In this example the pipette tip columns are constructed with a bottom frit only (pore size 105 μm) and filled with 80 μL of silica resin. Position 5 holds a 96-well plate filled with 250 μL Precipitation Buffer in each well. Positions 6 and 7 contain plates holding lysis and resuspension buffers, respectively. Positions 8, 11 and 12 contain buffers for wash 1, wash 2 and wash 3, respectively. In this procedure, wash 3 is the same solution as wash 2. Each of these is a deep-well block holding 500 μL of buffer. A deep-well block holding 300 μL Equilibration buffer is placed in position 9. The deep-well plate holding the cell pellets is placed at position 10. There is a UV-readable plate at position 13 to receive the purified plasmid DNA. Stations 14 and 15 can be used for drawing air through the pipette tip columns with vacuum and a UV plate reader resides at position 16.

The plate was processed as follows.
1. Resuspend cells. Transfer 150 ul resuspension buffer to cell pellet. 130 ul, 8-16 cycles, 10 ml/min.
2. Lyse cells. Add 150 uL of Lysis buffer to resuspended cells. 8 cycles of 180 μL at 10 ml/min with 2 sec pause.
3. Add 210 μL precipitation buffer. 8 cycles of 180 μL at 10 ml/min with 2 sec pause.
4. Attach pipette tip columns to the 96-channel head. Equilibrate the pipette tip columns. 2 cycles of 180 μL, 0.5 ml/min with 5 sec pause.
5. Capture
   a. Aspirate 200 μL air at 0.25 ml/min with 2 sec pause
   b. Submerge pipette tip column in unclarified lysate and expel 200 μL air at 0.25 ml/min with 2 sec pause. Particulates should float.
   c. Capture. 180 μL of unclarified lysate, 14 cycles at 0.25 ml/min with 20 sec pause.
6. Wash 1. 180 μL of wash buffer 1, 2 cycles at 0.5 ml/min with 10 sec pause.
7. Wash 2. 180 μL of wash buffer 2, 2 cycles at 0.5 ml/min with 10 sec pause.
8. Wash 3. 180 μL of wash buffer 2, 2 cycles at 0.5 ml/min with 10 sec pause.
9. Vacuum dry. Deposit tips to vacuum station and vacuum air through the tips for 5 min.
10. Elution
    a. Aspirate 70 μL of air.
    b. Engage tips and aspirate 130 μL of elution buffer at 0.25 ml/min.
    c. Incubate 5 min.
    d. Expel 130 μL of purified plasmid at 0.25 ml/min.

TABLE 6

Solutions

| Buffer Name | Content |
|---|---|
| Resuspension buffer | 50 mM Tris-HCl pH 8.0, 10 mM EDTA, 0.4 mg/mL RNase A |
| Lysis buffer | 200 mM NaOH, 2.5% SDS |
| Precipitation buffer | (A) 0.9M Potassium acetate pH 4.5 (B) 4.2M Guanidinium-HCl |
| Equilibration Solution | Water |
| Wash buffer | 100 mM TRIS-HCl pH 7.5, 65% Ethanol |
| Elution buffer | 10 mM Tris, pH 8.5 |

Example 6

Procedure for Midi-Prep of *E. Coli* Plasmid DNA from 96 Samples at a Time

The buffers used in this example are listed in Table 6.
1) In 10 mL of LB or Agencourt Ale medium, inoculate a single colony.
2) Grow overnight. 37° C., 16 hours at 300 rpm.
3) Centrifuge for 25 minutes at 3000 rpm.
4) Discard the supernatant.
5) Resuspend pellet with 150 μl Resuspension buffer.
6) Add 1 mL of Lysis buffer. Mix thoroughly.
7) Add 1.4 mL of Precipitation buffer. Mix thoroughly.
8) Attach pipette tip columns to the ME/MEA and equilibrate in 500 uL of Equilibration solution. The columns contain a 300 μL bed in a 1 mL pipette tip (2 cycles at 0.5 ml/min)
9) Intake 1 mL air into the column at a flow rate of 0.5 ml/min.
10) Move the pipette tip column to the bottom of the precipitated sample.
11) Expel 1 mL of air at 10 ml/min.
12) Capture plasmid by performing 10-15 cycles (0.25 ml/min or 0.5 ml/min).
13) Five wash steps. Move the pipette tip columns into a deep well block containing 1 mL of wash buffer. 4 cycles (0.5-5 ml/min).
14) Air dry. Use vacuum pump. 5-15 minutes.
15) Move the pipette tip columns into the deep well block containing elution buffer.
16) Intake 1333 μl, wait 5 min and expel.

Example 7

Midi-prep of *E. Coli* Plasmid DNA Using a Combination of Back and Forth Flow and Gravity Flow In this example, the midi-prep is performed as described in the preceding example except the wash and elution steps are done using gravity flow. The column is washed with 1 ml of buffer and the wash step is repeated 10-15 times. For the elution step, 1.2 mL of elution buffer is used.

Example 8

Midi-prep of *E. Coli* Plasmid DNA Using Gravity Flow

In this example, the midi-prep is performed as described in the preceding example except the capture step is performed using gravity flow.

Example 9

Extraction of DNA from Agarose Gel

The nucleic acids in this example are not limited to plasmid DNA. This procedure can be used to isolate nucleic acids of any type or size distribution that can be visualized on a gel. Agarose gel electrophoresis is the most common method for size separation and visualization of double stranded DNA. Agarose gels are used to separate DNA based on the mass (and thus, the length) of the DNA. Shorter DNA migrates farther through the gel compared to a long DNA. In practice, agarose gels are used to purify PCR products away from free primers, dNTPs, DNA polymerase and buffer components. The PCR product will migrate as a discreet band. Restriction digests of plasmids, for example, also result in discreet bands that can be purified by agarose gel. Discreet bands correspond to DNA of the same length. To utilize this separation as a pre-purification tool, the band corresponding to the DNA length of interest is excised from the gel using a scalpel or razor blade. The band is weighed and is placed into a microfuge tube. Three volumes of gel extraction buffer (50 mM MOPS pH 7.0, 1M NaCl, 15% (v/v) isopropanol) is added to the excised gel using the conversion 1 mg=1 μL. The tube is incubated at 50° C. for 10 minutes. The tube is vortexed every 2 to 3 minutes during this incubation. One volume of isopropanol is added to the tube.

A plasmid DNA pipette tip purification column is used to capture the DNA. The column is processed by the PhyNexus ME/MEA personal purification instrument. The MEA engages the pipette tip column and equilibrates it with 2 cycles of backand-forth flow in water using a flow rate of 0.5 mL/min and 20 second pauses at the end of each aspirate and dispense step. Next, the column captures the extracted DNA. This is accomplished using 4-20 cycles of back-and-forth flow at a flow rate of 0.25 mL/min and 20 second pauses at the end of each aspirate and dispense step. The columns are subject to a wash in 0.5 mL Wash Buffer (80% ethanol, 10 mM Tris-HCl pH 7.5). The wash is repeated in fresh buffer an additional two times. After washing, the pipette tip columns are transferred to a vacuum block and subject to 5 minutes of vacuuming to dry the columns to remove residual Wash Buffer components. The MEA next engages the pipette tip columns and aspirates 130 µL of water and incubates for 5 minutes. This is dispensed to release the plasmid DNA and a second elution is performed if necessary.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such preferred embodiments.

What is claimed is:

1. An automated method for capturing plasmid DNA from an unclarified lysate with a pipette tip column, the method comprising:
   a) providing a multi-well plate, wherein a plurality of wells in the multi-well plate contain unclarified lysates having a sample volume, wherein each unclarified lysate is comprised of plasmid DNA, liquid and particulates;
   b) providing a plurality of pipette tip columns arranged in a 9 mm center-to-center format wherein each pipette tip column is comprise of
      i) a column body having an open upper end,
      ii) an open lower end,
      iii) an open channel between the open upper end and the open lower end,
      iv) a bottom frit extending across the open lower end, and
      v) a solid phase positioned inside the open channel and above the bottom frit;
   c) engaging the open upper end of the pipette tip columns with a pump, wherein the pump is a syringe pump or the head of a robotic liquid handler;
   d) submerging the open lower end of the pipette tip columns in the unclarified lysates;
   e) aspirating and expelling a portion of the unclarified lysates through the open lower end of the pipette tip columns, wherein the portion of each unclarified lysate aspirated is between 10% and 80% of the sample volume;
   f) aspirating and expelling a wash solution through the open lower end of the pipette tip columns;
   g) transferring the pipette tip columns into a custom 9 mm center-to-center block, wherein the block is comprised of channels and wherein each channel is comprised of a seal, wherein the channels completely surround each individual pipette tip column over substantially the length of the column, and whereby each individual pipette tip column is sealed within a channel; and
   h) applying software-controlled vacuum through the block, wherein the vacuum is applied evenly through each pipette tip column.

2. The method of claim 1, wherein the portion of the unclarified lysate is between 10% and 60% of the sample volume.

3. The method of claim 1, wherein the method is performed on at least 2 and at most 96 pipette tip columns simultaneously.

4. An automated method for capturing plasmid DNA from an unclarified lysate with a pipette tip column, the method comprising:
   a) providing a multi-well plate, wherein a plurality of wells in the multi-well plate contain unclarified lysates having a sample volume, wherein each unclarified lysate is comprised of plasmid DNA, liquid and particulates;
   b) providing a plurality of pipette tip columns arranged in a 9 mm center-to-center format wherein each pipette tip column is comprised of
      i) a column body having an open upper end,
      ii) an open lower end,
      iii) an open channel between the open upper end and the open lower end,
      iv) a bottom frit extending across the open lower end, and
      v) a solid phase positioned inside the open channel and above the bottom frit;
   c) engaging the open upper end of the pipette tip columns with a pump, wherein the pump is a syringe pump or the head of a robotic liquid handler;
   d) submerging the open lower end of the pipette tip columns in the unclarified lysates;
   e) aspirating and expelling a portion of the unclarified lysates through the open lower end of the pipette tip columns, wherein the portion of each unclarified lysate aspirated is between 10% and 80% of the sample volume;
   f) aspirating and expelling a wash solution through the open lower end of the pipette tip columns;
   g) transferring the pipette tip columns into a custom 9 mm center-to-center block, wherein the block is comprised of channels, wherein the channels are comprised of a seal, whereby the channels completely surround each individual pipette tip column and whereby each column is sealed within a channel, and wherein the block is designed to apply vacuum evenly through all the pipette tip columns; and
   j) applying software-controlled vacuum through the block, wherein the vacuum is applied evenly through each pipette tip column.

5. The method of claim 4, wherein the portion of the unclarified lysate is between 10% and 60% of the sample volume.

6. The method of claim 4, wherein the method is performed on at least 2 and at most 12 pipette tip columns simultaneously.

* * * * *